United States Patent
Greiser et al.

(10) Patent No.: US 11,854,189 B2
(45) Date of Patent: Dec. 26, 2023

(54) DENTAL OVERVIEW MAP COMPILATION

(71) Applicant: Siemens Healthcare GmbH, Erlangen (DE)

(72) Inventors: Andreas Greiser, Erlangen (DE); Lars Lauer, Neunkirchen (DE); Rene Kartmann, Nuremberg (DE); David Grodzki, Erlangen (DE); Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 446 days.

(21) Appl. No.: 17/104,309

(22) Filed: Nov. 25, 2020

(65) Prior Publication Data

US 2021/0158514 A1 May 27, 2021

Related U.S. Application Data

(60) Provisional application No. 62/941,179, filed on Nov. 27, 2019.

(51) Int. Cl.
*A61B 5/055* (2006.01)
*G06T 7/00* (2017.01)
*A61B 5/00* (2006.01)

(52) U.S. Cl.
CPC .......... *G06T 7/0012* (2013.01); *A61B 5/055* (2013.01); *A61B 5/4547* (2013.01);
(Continued)

(58) Field of Classification Search
CPC ......... G06T 7/0012; G06T 2207/10088; G06T 2207/30036; A61B 5/055; A61B 5/4547;
(Continued)

(56) References Cited

U.S. PATENT DOCUMENTS

2007/0030346 A1  2/2007  Feuerlein
2013/0252196 A1  9/2013  Hell et al.
(Continued)

OTHER PUBLICATIONS

Cankar, Ksenija et al.: "T2 Mapping as a Tool for Assessment of Dental Pulp Response to Caries Progression: An in vivo MRI Study"; Caries Research; Bd. s54; Nr. 1; 11. Sep. 2019; pp. 24-35, XP055792578, CH; ISSN: 0008-6568; DOI: 10.1159/000501901 Gefunden im Internet: URL:https://www.karger.com/Article/Pdf/501901.
(Continued)

*Primary Examiner* — Dixomara Vargas
(74) *Attorney, Agent, or Firm* — Banner & Witcoff Ltd.

(57) ABSTRACT

A method for compiling a dental overview map of the dentition of an examination object on the basis of magnetic resonance (MR) data from a MR measurement of the dentition. Performing an MR measurement for acquiring MR data from the dentition. Performing an analysis of sections of the dentition in order to determine an abnormality on the basis of the MR data, wherein a section of the dentition includes a subset of the number of teeth in the dentition, and determining an abnormality in at least one section. Compiling a dental overview map as a function of the MR data and the abnormality of the at least one section of the dentition. Providing the dental overview map.

12 Claims, 4 Drawing Sheets

(52) U.S. Cl.
CPC ........ *A61B 5/4842* (2013.01); *A61B 2576/00* (2013.01); *G06T 2207/10088* (2013.01); *G06T 2207/30036* (2013.01)

(58) Field of Classification Search
CPC . A61B 5/4842; A61B 2576/00; A61B 5/1076; A61B 5/0033; A61B 5/4552; G01R 33/4816
See application file for complete search history.

(56) References Cited

U.S. PATENT DOCUMENTS

| | | | |
|---|---|---|---|
| 2014/0084920 A1 | 3/2014 | Maerzendorfer et al. | |
| 2015/0305669 A1 | 10/2015 | Hultgren | |
| 2019/0147648 A1* | 5/2019 | Wolff | A61B 6/5247 433/213 |
| 2019/0231492 A1* | 8/2019 | Sabina | A61B 1/0646 |

OTHER PUBLICATIONS

Tymofiyeva, Olga et al: "High-resolution 3D magnetic resonance imaging and quantification of carious lesions and dental pulp in vivo"; Magnetic Resonance Materials in Physics, Biology and Medicine; Bd. 22; Nr. 6; 19. Nov. 2009; pp. 365-374; XP055792816; DE,GB; ISSN: 0968-5243; DOI: 10.1007/s10334-009-0188-9; Gefunden im Internet: URL:http://link.springer.com/article/10.1007/s10334-009-0188-9/fulltext.html.

Bracher, Anna-Katinka et al.: "Feasibility of ultra-short echo time (UTE) magnetic resonance imaging for identification of carious lesions : MRI for Identification of Carious Lesions"; Magnetic Resonance in Medicine; Bd. 66; Nr. 2, 28. Feb. 2011; pp. 538-545; XP055792794; US; ISSN: 0740-3194; DOI: 10.1002/mrm.22828 Gefunden im Internet: URL:https://api.wiley.com/onlinelibrary/tdm/v1/articles/10.1002%2Fmrm.22828.

European Search Report dated Apr. 21, 2021 for European U.S. Appl. No. 20/202,947.

Löffler R. et. al., "Localized Spectroscopy from Anatomically Matched Compartments: Improved Sensitivity and Localization for Cardiac 31P MRS in Humans", Journal of Magnetic Resonance 134, pp. 287-299, 1998.

* cited by examiner

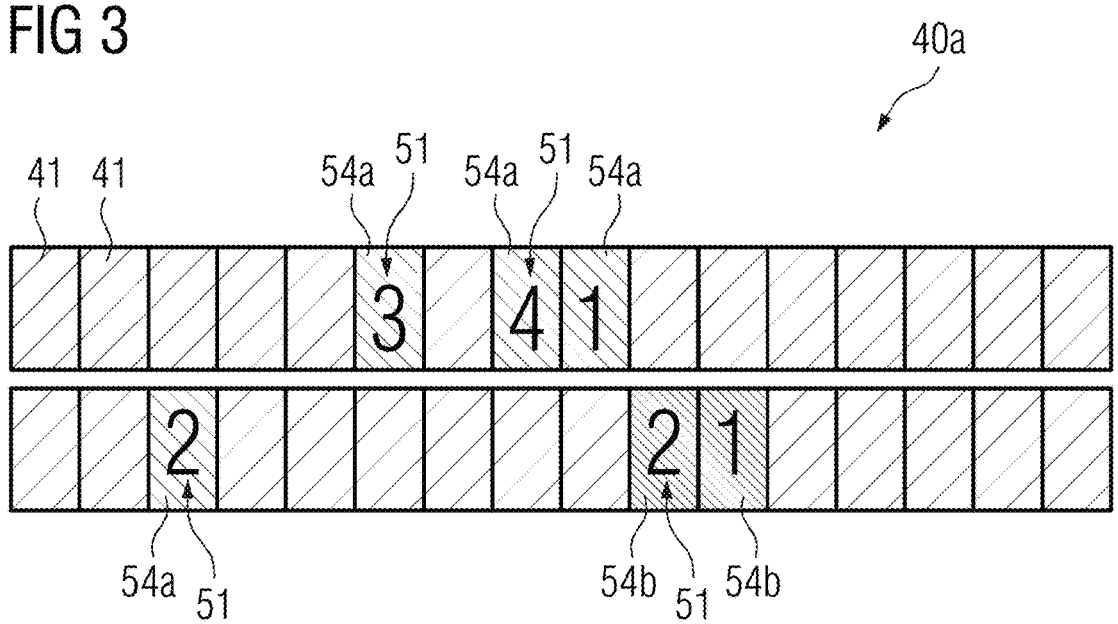
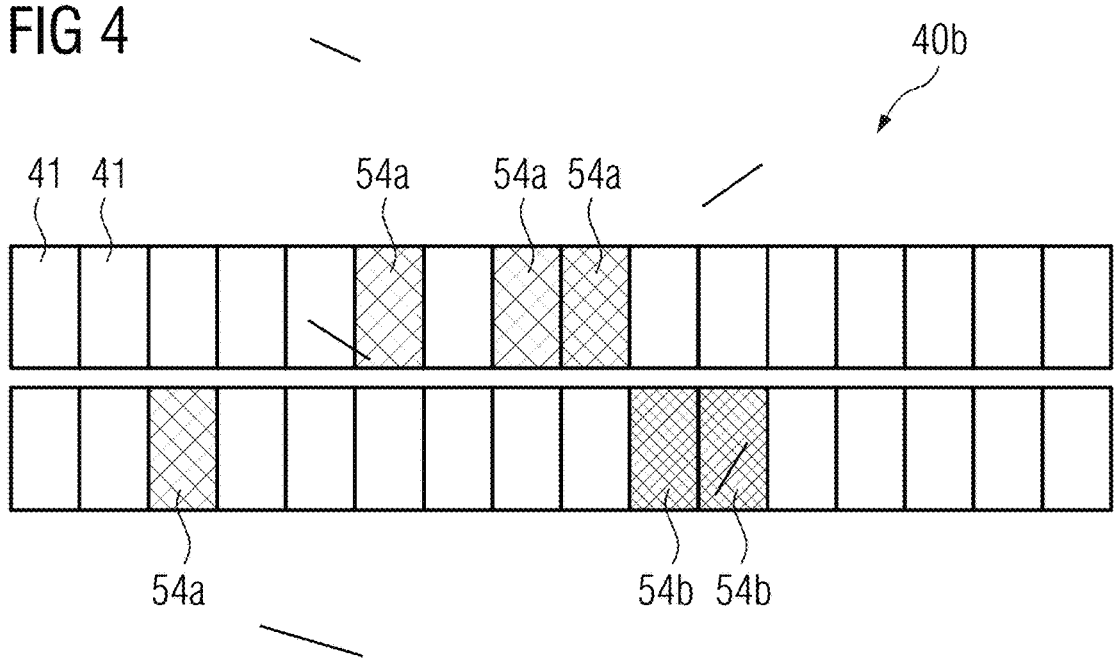

DENTAL OVERVIEW MAP COMPILATION

TECHNICAL FIELD

The disclosure relates to a method for compiling a dental overview map of the dentition of an examination object. The disclosure further relates to a magnetic resonance apparatus with a computing unit and a computer program product which can be loaded directly into a data storage device of a computing unit of a magnetic resonance apparatus in order to carry out a method according to the disclosure.

BACKGROUND

At present, diseases of the teeth and of periodontium, such as, for example, caries or periodontitis, are usually diagnosed with X-ray based imaging methods. This is primarily done using conventional or digital X-ray projection methods and recently also three-dimensional X-ray methods. One example of a three-dimensional X-ray method is digital volume tomography which can be used for imaging teeth and the viscerocranium.

A major disadvantage of X-ray methods is the need to use ionizing radiation for the imaging. Magnetic resonance tomography is an imaging method that avoids ionizing radiation. This typically enables better soft-tissue contrast than X-ray methods and is used as standard to support three-dimensional imaging of an examination object. Hence, magnetic resonance tomography is a potential alternative to known X-ray methods for imaging dentition and/or the jaw region and for diagnosing dental diseases in the examination object.

Magnetic resonance tomography is a known imaging method with which magnetic resonance images of the interior of the examination object can be generated. For the performance of a magnetic resonance measurement, the examination object is usually positioned in a strong, static and homogeneous basic magnetic field (B0 field) of a magnetic resonance apparatus. The basic magnetic field can have magnetic field strengths of from 0.2 tesla to 7 tesla such that nuclear spins of the examination object align along the basic magnetic field. To trigger so-called nuclear magnetic resonances, radio-frequency excitation pulses are radiated into the examination object. Every radio-frequency excitation pulse causes certain nuclear spins of the examination object to deviate from the basic magnetic field by an amount that is also known as the flip angle. Herein, a radio-frequency excitation pulse can have a magnetic alternating field with a frequency corresponding to the Larmor frequency at the respective static magnetic field strength. The excited nuclear spins can have a rotating and decaying magnetization (nuclear magnetic resonance) which can be detected by means of special antennas. For spatial encoding of the nuclear magnetic resonances of the examination object, magnetic gradient fields can be superimposed on the basic magnetic field.

The received nuclear magnetic resonances are typically digitized and stored as complex values in a k-space matrix. This k-space matrix can be used as the basis for the reconstruction of magnetic resonance images and the determination of spectroscopy data. A magnetic resonance image is typically reconstructed by means of a multidimensional Fourier transform of the k-space matrix.

Due to the avoidance of ionizing radiation, magnetic resonance tomography is in particular suitable for continuous diagnostic monitoring of dental diseases and/or odontogenesis in the context of a longitudinal imaging study. Longitudinal imaging studies usually entail a plurality of imaging examinations in order to determine the progression of a disease or the outcome of therapeutic treatment over a predetermined duration. However, herein, magnetic resonance tomography has the disadvantage of increased duration which is usually associated with the recording of magnetic resonance data from the examination object. This can in particular be problematic with pediatric patients since patient movements during the imaging examination could cause image artifacts which impair the quality of the magnetic resonance images. The increased duration associated with the acquisition of magnetic resonance data can further be a problem when treating a large number of patients who are usually treated by dental health facilities.

SUMMARY

It is therefore an object of the disclosure to improve the efficiency of imaging of the dentition of an examination object.

This object is achieved according to the disclosure by the subject matter of the independent claims. Advantageous aspects and expedient developments are the subject matter of the dependent claims.

In the method according to the disclosure, a dental overview map of the dentition of an examination object is compiled on the basis of magnetic resonance data from a magnetic resonance measurement of the dentition. Depending on a condition of the examination object, the examination object's dentition can include a part of a tooth, an interdental space, one tooth, a plurality of teeth, a dental arch or a plurality of dental arches. A dental arch typically comprises the periodontium or a part of the periodontium with all the teeth or some of the teeth in the upper jaw or the lower jaw the examination object. The dentition preferably includes all the teeth in the upper jaw and of the lower jaw of the examination object.

A magnetic resonance measurement is preferably a recording of nuclear magnetic resonances of the examination object by means of a magnetic resonance apparatus. The recorded nuclear magnetic resonances can be digitized and stored as a k-space matrix, the so-called magnetic resonance data. It is conceivable for the magnetic resonance measurement to be variable as a function of imaging parameters. For example, a position of an imaging volume, a dimension of the imaging volume, an excitation duration, an echo time, a repetition time or further imaging parameters of the magnetic resonance measurement can be adapted in order to acquire magnetic resonance data of a diagnostically relevant region of the dentition. The imaging parameters of the magnetic resonance measurement can be combined in a so-called imaging sequence which is able to determine a course of the magnetic resonance measurement, such as, for example, the number and temporal sequence of radio-frequency excitation pulses. It is conceivable for the magnetic resonance data to be used to reconstruct magnetic resonance images of the examination object's dentition.

In one step of the method according to the disclosure, a magnetic resonance measurement for acquiring magnetic resonance data from the dentition is performed, wherein an imaging volume of the magnetic resonance measurement is matched with a volume of the dentition and wherein the imaging volume includes a number of teeth in the dentition. An imaging volume can be a volume of any shape within an image-recording region of the magnetic resonance apparatus from which nuclear magnetic resonances of the examination object can be received. For the magnetic resonance measurement, the examination object is preferably positioned in the image-recording region of the magnetic resonance apparatus such that at least one part of a volume of the examination object's dentition matches the imaging volume. Herein, the imaging volume is in particular matched to the volume of the dentition such that a diagnostically relevant region of the dentition is positioned within the imaging volume. In one example, the imaging volume can be matched with the volume of the dentition such that the imaging volume includes a number of teeth, For example, one tooth, two teeth, three teeth or a plurality of teeth. Herein, the number of teeth can include one tooth or a plurality of teeth in the upper jaw and/or the lower jaw. The imaging volume can have any shape. In a preferred aspect, the imaging volume has a spherical or an ovoid shape. However, it is also conceivable for the imaging volume to have a polygonal shape or result from a combination of an ovoid shape and a polygonal shape. As described above, during the acquisition of the magnetic resonance data from the dentition, a k-space matrix is recorded with the nuclear magnetic resonances of the number of teeth positioned in the imaging volume.

In a further step of the method according to the disclosure, in order to determine an abnormality, an analysis of sections of the dentition each of which include a subset of the number of teeth in the dentition is performed on the basis of the magnetic resonance data, wherein an abnormality is determined in at least one section. A section can be any subset of the number of teeth in the dentition. Preferably, a section includes exactly one tooth, exactly two teeth or a predetermined number of teeth in the dentition. However, it is also conceivable for a section to be a part of a tooth. For example, a section can be defined by a grid that divides the volume of the dentition into uniform or non-uniform grid elements. Herein, a section can be exactly one grid element or a plurality of grid elements. In another example, a section can be the smallest resolvable picture element (pixel) or a multiple of a picture element of a magnetic resonance image reconstructed from the magnetic resonance data. Preferably, the volume of the dentition is divided into a plurality of sections in order to facilitate the determination of abnormalities and/or further processing and/or depiction of the abnormalities. Herein, the analysis of the dentition is in particular performed section-by-section until all the sections of the dentition have been analyzed.

It is also conceivable for the analysis of the sections of the dentition to take place on the basis of magnetic resonance images reconstructed as a function of the magnetic resonance data from the dentition. The determination of abnormalities can, for example, take place as a function of contrasts of single or multiple picture elements of a magnetic resonance image. It is also conceivable for characteristic structures which can be assigned to an anatomical structure and/or abnormality to be derived from the contrasts of a plurality of picture elements. Preferably, an image-processing unit is used for the determination of abnormalities. The image-processing unit can be embodied to identify characteristic structures automatically on the basis of contrasts of picture elements of a magnetic resonance image and/or volume elements (voxels) of a three-dimensional data set of magnetic resonance images. The determination of abnormalities can further include the use of an intelligent algorithm, such as, for example, a neural network, an expert system, an optimization method, a deep learning method or the like. Intelligent algorithms can be configured to determine abnormalities as a function of further information, such as, for example, training images, magnetic resonance images with classified abnormalities and contrast templates with typical contrasts or reference values for abnormalities. The analysis of the sections of the dentition enables quantitative and/or qualitative information on a tooth and/or the number of teeth. For example, the information can comprise a statement regarding the teeth affected by dental disease and/or the degree of the dental disease. Herein an abnormality is determined in at least one section of the dentition. Furthermore, a condition of the examination object's dentition can be derived from the information from all sections of the dentition.

In a further step of the method according to the disclosure, a dental overview map is compiled as a function of the magnetic resonance data and the abnormality of the at least one section of the dentition, wherein the dental overview map comprises a representation of a tooth in the examination object's dentition and a representation of the abnormality of the at least one section of the dentition. Preferably, the dental overview map includes a structured depiction of the number of teeth in the examination object's dentition. Herein, a tooth can, for example, be plotted as a function of relative position to a dental arch and/or to further teeth of the examination object and be given numbering and/or an identifier providing information on the type and/or position of the tooth in the examination object's dentition.

The dental overview map in particular comprises a representation of a tooth or the number of teeth. A representation can include any schematized depiction of a tooth and/or the number of teeth. It is furthermore conceivable for the dental overview map to include magnetic resonance images or segments of magnetic resonance images of a tooth and/or the number of teeth. Preferably, the information on the type and/or position of the tooth in the dentition is determined on the basis of contrasts or signal intensities of the picture elements of the magnetic resonance images. The magnetic resonance images can furthermore be linked to the representation of the number of teeth and/or the numbering and/or the identifier.

The dental overview map further comprises a representation of the abnormality of the at least one section of the dentition. Such a representation can, for example, include a marking and/or a color highlighting of the abnormality in the magnetic resonance images of the number of teeth. However, it is also conceivable for the representation of the abnormality to include an indication, such as, for example, a text field, a geometric object, a numerical digit, a symbol, a marking or any combination of such indications. In one example, a tooth with an abnormality and/or an abnormality of the tooth is provided on the dental overview map with an indication showing or encoding information on the type of tooth, the presence of dental disease and/or a degree of the dental disease, such as, for example, a state of progress of the dental disease. In one preferred aspect, sections of the dentition with an abnormality are marked and/or highlighted during the compilation of the dental overview map. Herein, an abnormality can be provided with an indication containing information on the abnormality.

In one step of the method according to the disclosure, the dental overview map is provided. The provision can, for example, include outputting the dental overview map on any desired display unit. It is conceivable for the dental overview map to be output on a screen of the magnetic resonance apparatus. Herein, outputting the overview map on a screen of the magnetic resonance apparatus can support an attending medical practitioner, such as, for example, a dentist or an oral surgeon in the evaluation of the condition of the examination object's dentition. For example, the dental overview map can contain a schematized representation of teeth with abnormalities which gives the attending medical practitioner a pointer toward which teeth require more detailed examination. One example of this is the schematized depiction of the initial stage of dental caries of a tooth. The dental overview map can also alert the attending medical practitioner of abnormalities which are difficult to diagnose by a purely visual inspection of the dentition. Such abnormalities can, for example, be cysts or inflammation in the region of the root of a tooth.

The dental overview map can further be output on the screen of a mobile device, such as, for example, a smartphone or a tablet. In one aspect, the examination object is a patient, wherein the dental overview map is transmitted to the patient's private mobile device in the context of informing the patient and/or documenting the condition of the patient's dentition. The mobile device can have a corresponding app or software application which is embodied to output the dental overview map by means of a screen of the mobile device to a user of the mobile device. The app can further comprise an instruction for supporting cleaning of the teeth and/or be coupled to a corresponding app for supporting cleaning of the teeth. This can advantageously inform the user of the mobile device of the condition of the dentition and/or indicate that special caution should be taken when cleaning dental regions with an abnormality.

It is also conceivable for the provision of the dental overview map to include storing the dental overview map in a data storage device. The data storage device can be embodied to store a plurality of dental overview maps and make them available to the attending medical practitioner and/or the examination object. In one aspect, the magnetic resonance apparatus comprises a computing unit embodied to retrieve a first dental overview map or a plurality of dental overview maps of the examination object from a data storage device and to parameterize a magnetic resonance measurement as a function of the dental overview map or the plurality of dental overview maps. The parameterization of the magnetic resonance measurement can, for example, include setting an imaging sequence or an imaging parameter of a subsequent magnetic resonance measurement.

The method according to the disclosure can the offer the advantage of enabling efficient and reproducible imaging of the dentition of an examination object by means of a magnetic resonance apparatus. Another conceivable advantage is that automatic ascertaining of abnormalities in the number of teeth and the compilation of a dental overview map for documenting the condition of the dentition advantageously enable the duration and/or effort required for the compilation of data needed for a quantitative and qualitative evaluation of the condition of the dentition to be reduced.

In one possible aspect of the method according to the disclosure, the at least one section in which the abnormality is determined is a first section, wherein, during the performance of the analysis of sections of the dentition, the presence of an abnormality in a second section is excluded. Exclusion of the presence of an abnormality can mean that the subset of the number of teeth in the second section have no abnormalities. Hence, the subset of the number of teeth in the second section can comprise a healthy tooth. It is in particular conceivable for the subset of the number of teeth in the second section not to comprise any abnormality typical of dental disease, the malalignment of a tooth and/or damage to a tooth. Preferably, during the compilation of the dental overview map, the first section with the abnormality is highlighted compared to the second section. This can, for example, take place by means of an indication, an identifier and/or a colored marking.

The exclusion of abnormalities in one or more sections of the dentition can advantageously expedite the evaluation of the condition of the examination object's dentition. Further, the condition of the dentition can be documented by means of the dental overview map on the basis of information on sections with abnormalities and sections without abnormalities. This can advantageously be used as the basis for the provision of a planning guide for subsequent imaging examinations, for example in the context of long-term dental caries therapy, an orthodontic measure and/or a longitudinal imaging study.

In one possible aspect of the method according to the disclosure, the performance of the analysis of sections of the dentition includes a determination of inflammation and/or dental caries. For the determination of inflammation, an imaging parameter and/or an imaging sequence of the magnetic resonance measurement can be set such that high soft-tissue contrast of the magnetic resonance data and/or the magnetic resonance images is obtained. This enables inflammation of soft tissue, such as, for example, the gingival tissue or oral mucosa, to be reliably identified. It is conceivable for the spatial resolution of the magnetic resonance measurement to be reduced during the determination of inflammation due to the high soft-tissue contrast of the magnetic resonance measurement. Spatial resolution is typically defined by a number of picture elements of an image section of the magnetic resonance image. Reduced spatial resolution can, for example, be present if a dimension of the picture element corresponds to a dimension of a few hundred micrometers to a few millimeters of a mapped anatomy. The determination of inflammation can in particular take place in the context of the planning and/or aftercare of a surgical intervention, such as, for example, root canal treatment.

Further, the performance of the analysis of the sections of the dentition can also include a determination of dental caries and/or a cyst in a surrounding area of the number of teeth. It is conceivable for the determination of the cyst on a tooth or a jaw region of the examination object also to take place on the basis of magnetic resonance data and/or magnetic resonance images with high soft-tissue contrast. On the other hand, dental caries can be reliably identified on the basis of a difference in contrast from the dental enamel or the dentin of a tooth. The difference in contrast can, for example, be effected as a result of different relaxation time of a section affected by dental caries section compared to healthy dental enamel or dentin. Hence, for the determination of dental caries, the magnetic resonance measurement can comprise an imaging parameter and/or an imaging sequence usually used for imaging very solid tissue. In addition to inflammation and dental caries, the analysis of the sections of the dentition is obviously able to determine a large number of further abnormalities. Possible examples of abnormalities include a malposition of a tooth, a displacement of a tooth in the context of an orthodontic measure, periodontitis, a damaged and/or fractured tooth, wisdom tooth progression in a jaw region and the like.

The high soft-tissue contrast of the magnetic resonance measurement enables the presence of inflammation and/or a cyst to be determined quickly and reliably. As a result, treatment can be initiated in good time during aftercare following dental treatment, such as, for example, root canal treatment. In particular during the identification of inflammation of soft tissue of the dentition, the acquisition of the magnetic resonance data can advantageously take place with a coarse resolution thus enabling the duration required to perform the magnetic resonance measurement to be reduced.

In one aspect, the method according to the disclosure includes a further step in which a relative position between an abnormality of the at least one section and at least one tooth with the at least one section is determined, wherein the compilation of the overview map takes place as a function of the relative position between the abnormality of the at least one section and the at least one tooth. Herein, the at least one section with the abnormality can be present on one tooth or extend over a plurality of teeth. The determination of the relative position between the abnormality in the at least one section and the at least one tooth can, for example, take place on the basis of positional information on the abnormality and the at least one tooth. Positional information can include a coordinate or a plurality of coordinates in a coordinate system defined by the imaging volume. In a simple example, a first coordinate depicts an area centroid or volume centroid of the abnormality while a second coordinate depicts an area centroid or volume centroid of the at least one tooth. The relative position between the abnormality of the at least one section and the at least one tooth can be determined by correlating the first coordinate and the second coordinate in the imaging volume. It is also conceivable for the positional information coordinates to comprise a plurality of points distributed along a contour of the abnormality and/or a contour of the at least one tooth, for example. The plurality of points can define an area, a volume and/or a position of the abnormality and the at least one tooth in the imaging volume which can be used to determine the relative position between the abnormality of the at least one section and the at least one tooth.

Preferably, the positional information on the abnormality and/or the at least one tooth is determined on the basis of contrasts of the magnetic resonance image or of signal intensity values of the magnetic resonance data. A spatial assignment of individual picture elements of the magnetic resonance image to the imaging volume can, for example, take place on the basis of frequency encoding, phase encoding and spatial encoding which are obtained by applying gradient fields during the performance of the magnetic resonance measurement. The determination of the positional information preferably takes place by means of an image-processing unit. The image-processing unit can further be embodied to determine the relative position between the abnormality and the at least one tooth on the basis of the positional information on the abnormality and the at least one tooth.

The compilation of the dental overview map takes place as a function of the relative position between the abnormality of the at least one section and the at least one tooth. For example, during the compilation of the dental overview map, a representation of the abnormality is positioned relative to the representation of the at least one tooth such that a position of the representation of the abnormality at least approximately matches an anatomically correct position of the abnormality on the at least one tooth.

The determination of the relative position between the abnormality of a section and the at least one tooth of the section advantageously enables a representation of the abnormality to be depicted in an approximately correct position relative to the representation of the number of teeth by means of the dental overview map. The use of a corresponding dental overview map can advantageously reduce the risk of an incorrect diagnosis compared to the use of a magnetic resonance image since a difference in contrast between a healthy tooth and a diseased tooth in the magnetic resonance images, in particular in the initial stage of dental disease, can be small.

In a further aspect of the method according to the disclosure, the magnetic resonance measurement is a first magnetic resonance measurement which, for acquiring first magnetic resonance data, is performed at a first time point, wherein a first imaging volume of the first magnetic resonance measurement is matched with a first volume of the dentition and includes a first number of teeth and wherein the at least one section in which the abnormality is determined is a first section. A first time point is preferably the start of diagnostic imaging of the examination object's dentition by means of the method according to the disclosure. For this, a first magnetic resonance measurement is performed with a first imaging volume which is matched with the first volume of the dentition. Herein, the first number of teeth of the first volume of the dentition can include a diagnostically relevant region such as, for example, one tooth, two teeth and a plurality of teeth in one or both dental arches of the examination object. The diagnostically relevant region can, for example, be based on a suspicion of the presence of dental disease and/or a visual evaluation of the condition of the dentition by the attending medical practitioner.

The first magnetic resonance measurement in particular comprises a first imaging sequence with first imaging parameters for acquiring first magnetic resonance data. The first imaging sequence can determine a first recording quality, such as, for example, a spatial resolution of the first magnetic resonance data. It is conceivable for the first recording quality to be set as a function of a suspicion of the presence of dental disease and/or the diagnostically relevant region. The first recording quality can, for example, be set by adapting a slice thickness and/or completeness of a recording of first magnetic resonance data (k-space data).

Preferably, the first imaging parameters of the first imaging sequence are stored together with the first magnetic resonance data and the dental overview map in a database. This information can be used as a reference in subsequent examinations, for example in the context of a so-called longitudinal imaging study of the dentition. It is conceivable for the first magnetic resonance measurement to have particularly high resolution, particularly high recording quality, a high number of different tissue contrasts and/or a particularly large imaging volume in order to acquire magnetic resonance data from all the examination object's teeth and provide a basis for a quantitative and qualitative evaluation of the condition of the dentition. Herein, a quantitative evaluation can be an evaluation of the degree of dental disease while a qualitative evaluation includes a diagnosis of the type of dental disease present.

In a further step of the method according to the disclosure, a second magnetic resonance measurement for acquiring second magnetic resonance data from the dentition is performed at a second time point, wherein a second imaging volume of the second magnetic resonance measurement is matched with a second volume of the dentition and includes at least one tooth and wherein at least one imaging parameter of the second magnetic resonance measurement is determined as a function of the abnormality of the first section. The second time point can directly follow the first time point. This can mean that the second magnetic resonance measurement is performed following the first magnetic resonance measurement. Hence, the difference between the first time point and the second time point can approximately correspond to the duration of the first magnetic resonance measurement. However, the second time point can also have a greater time interval from first time point. For example, the second magnetic resonance measurement can be a follow-up examination of a patient, wherein the first time point and the second time point are separated by at least a day, more than a week, more than a month, more than six months, nine to 15 months or more than 15 months. Preferably, the first magnetic resonance measurement and the second magnetic resonance measurement represent a longitudinal imaging study or part of longitudinal imaging study of the dentition of a patient. It is in particular conceivable for a third magnetic resonance measurement to follow the second magnetic resonance measurement at a third time point. Obviously, further magnetic resonance measurements at further time points are also conceivable. It is conceivable for imaging examinations to be performed at further time points with a different imaging method. Possible imaging methods are, example, X-ray projection methods, high-resolution X-ray computed tomography methods, intraoral cameras and and/or magnetic resonance methods with different scanner architectures. It is furthermore conceivable for the measurements to be performed at further time points with the same magnetic resonance apparatus, for example with a conventional radiological magnetic resonance apparatus or with a dedicated magnetic resonance apparatus which is embodied to acquire magnetic resonance data from the dentition of a patient. Preferably, a set of measurement data from subsequent imaging examinations is reduced in order to enable time-efficient imaging. For example, the imaging volume, the recording quality, the number of tissue contrasts and/or the completeness of the magnetic resonance data from further magnetic resonance measurements can be reduced as a function of measurement data and/or identified abnormalities from preceding imaging examinations in order to reduce the duration of subsequent imaging examinations.

During the performance of the second magnetic resonance measurement at least one imaging parameter is determined as a function of the abnormality of the first section. It is conceivable for a position and/or a dimension of the second imaging volume to be changed compared to the first imaging volume in order to adapt the second imaging volume to a volume of the dentition with the first section. Herein, one tooth or a plurality of teeth from a marginal region of the first imaging volume can be included in the second imaging volume or excluded from the second imaging volume. It is also conceivable for a second recording quality of the second magnetic resonance measurement to be adapted as a function of the abnormality of the first section. As described above, in the case of the presence of inflammation in the first section, the second recording quality can be reduced since a higher soft-tissue contrast of the second magnetic resonance measurement enables reliable quantification of the inflammation even in the case of low recording quality. However, it is also conceivable for the second recording quality to be increased compared to the first recording quality while a dimension of the second imaging volume is reduced compared to the first imaging volume. This enables a diagnostically relevant region to be depicted with high resolution while the duration of the second magnetic resonance measurement is reduced.

In one aspect, a first dental overview map is compiled as a function of the first magnetic resonance data and a second dental overview map is compiled on the basis of the second magnetic resonance data. However, it is also conceivable for a combined dental overview map to be compiled as a function of the first magnetic resonance data and the second magnetic resonance data. Herein, the combined dental overview map can compare the condition of the dentition such as, for example, an abnormality of the first section, at the first time point and the second time point.

The first magnetic resonance data from the first magnetic resonance measurement can advantageously be used to document abnormalities of the examination object's dentition. This information can be used in the context of continuous aftercare, in particular a longitudinal imaging study, in order to adapt imaging parameters of subsequent imaging examinations and advantageously increase the efficiency and/or quality of the subsequent imaging examinations. Multiple acquisition of magnetic resonance data at different time points can advantageously enable systematic quantitative evaluation of the condition of the examination object's dentition. Examples of an advantageous application of a longitudinal imaging study by means of the method according to the disclosure include a morphometric analysis of the gingival tissue in order to evaluate periodontitis and document a progression of dental disease and/or odontogenesis in the context of an orthodontic measure.

In one possible aspect of the method according to the disclosure, the second magnetic resonance measurement for acquiring second magnetic resonance data from the first section is performed with a second recording quality, wherein the second recording quality is higher than or equal to a first recording quality used during the performance of the first magnetic resonance measurement for the acquisition of the first magnetic resonance data from the first section.

It is conceivable for the second recording quality to be increased compared to the first recording quality in that the slice thickness of the second magnetic resonance measurement to be resolved is reduced compared to the first magnetic resonance measurement. This enables the number of volume elements and the spatial resolution of the second magnetic resonance measurement to be increased compared to the first magnetic resonance measurement. Herein, preferably, the second recording quality of the second magnetic resonance measurement is determined as a function of the abnormality of the first section of the first magnetic resonance measurement. Herein, the second recording quality is in particular determined such that the spatial resolution and/or signal-noise ratio of the second magnetic resonance data has sufficient sensitivity for a reliable evaluation of the development of the abnormality. It is conceivable for the second recording quality to be determined automatically by an image-processing unit of the magnetic resonance apparatus or input by a user of the magnetic resonance apparatus, such as, for example, the attending medical practitioner, by means of an input unit.

Increasing the second recording quality compared to the first recording quality advantageously enables the degree of detail of an abnormality to be increased. This enables the progression of the examination object's dental disease to be quantified more precisely thus reducing the risk of an incorrect evaluation of the degree of dental disease. The higher recording quality advantageously further enables the derivation of adapted measures for treating the dental disease present.

In one possible aspect of the method according to the disclosure, the performance of the second magnetic resonance sequence for acquiring second magnetic resonance data from the second section takes place with a third recording quality, wherein the third recording quality is lower than a first recording quality used during the performance of the first magnetic resonance measurement for the acquisition of the first magnetic resonance data from the first section. As described above, the second section can depict a subset of the number of teeth for which an abnormality has been excluded. Therefore, the second section can be ignored for an evaluation of the progression of dental disease in the first section. However, it is conceivable for dental disease to have developed in the second section of the examination object's dentition between the first time point and the second time point a dental disease. In order to exclude such dental disease, the second imaging volume of the second magnetic resonance measurement can also include a volume of the dentition with the second section. Herein, the acquisition of second magnetic resonance data from the second section takes place with a third recording quality which is reduced compared to the first recording quality. It is conceivable for the third recording quality to be reduced selectively, that is solely for a volume of the dentition with the second section. Here, it is, for example, possible to use a dedicated imaging sequence with a coarser spatial resolution. A preferred possibility for reducing the third recording quality compared to the second recording quality is to increase the slice thickness to be resolved. A further possibility for reducing the third recording quality compared to the first recording quality is in particular low-sample recording of nuclear magnetic resonances (k-space data) from the second section of the volume of the dentition.

It is furthermore conceivable for the second magnetic resonance data from the first section also to be acquired with reduced recording quality compared to the first magnetic resonance measurement such that the second recording quality is reduced compared to the first recording quality. For example, an anatomical compartment model that enables the reconstruction of second magnetic resonance data and/or second magnetic resonance images with low-sample low-resolution and/or acquired with a lower imaging volume to be compiled on the basis of the first magnetic resonance data with a higher spatial resolution. Further, the use of artificial intelligence, such as, for example, trained neural networks or deep learning methods, for the reconstruction of low-resolution and/or low-sample second magnetic resonance data and/or second magnetic resonance images is also conceivable.

Reducing the third recording quality compared to the first recording quality during the acquisition of second magnetic resonance data from the second section advantageously enables the duration of the performance of the second magnetic resonance measurement to be reduced. This can in particular be advantageous with pediatric patients who typically find it difficult to remain still for lengthy measurement periods.

In one possible aspect of the method according to the disclosure, the performance of the second magnetic resonance measurement for the acquisition of second magnetic resonance data from the first section takes place with a second recording quality and the performance of the second magnetic resonance measurement for the acquisition of second magnetic resonance data from the second section takes place with a third recording quality, wherein the second recording quality is higher than the third recording quality. In this aspect, the second magnetic resonance measurement of the first section and the second section is in each case performed with different imaging parameters or imaging sequences in order to acquire different recording qualities of the second magnetic resonance data from the first section and second magnetic resonance data from the second section. Preferably, herein, the slice thickness and/or the set of the nuclear magnetic resonances acquired are adapted such that the second recording quality of the first section is higher than the third recording quality of the second section.

Selective adaptation of the recording qualities of different sections advantageously enables the time efficiency of the second magnetic resonance measurement to be increased in that second magnetic resonance data from sections with abnormalities is acquired with increased resolution while sections for which an abnormality was excluded in the first magnetic resonance measurement are acquired with lower resolution.

In a further aspect of the method according to the disclosure, the second imaging volume of the second magnetic resonance measurement is restricted to the first section of the dentition. As described above, the second imaging volume can be determined as a function of the first magnetic resonance data and positional information on the abnormality. Herein, a dimension of the second imaging volume can in particular be reduced compared to a dimension of the first imaging volume in order to obtain adapted coverage of the first section of the dentition. It is also conceivable for a position of the second imaging volume to be changed relative to a position of the first imaging volume. Herein, the second imaging volume can be aligned toward a volume of the dentition which comprises the first section with the abnormality. Preferably, the second section and/or further sections without abnormalities are excluded from the second imaging region of the second magnetic resonance measurement.

Selective acquisition of nuclear magnetic resonances of the first section of the dentition can, for example, take place using a receiving antenna positioned locally on the first section of the dentition. It is furthermore conceivable for the k-space data from the second magnetic resonance measurement to include nuclear magnetic resonances from a larger imaging volume, but the extraction of second magnetic resonance data to be limited to the first section of the dentition. Selective extraction of the second magnetic resonance data from the k-space data can, for example, take place on the basis of frequency encoding, phase encoding and/or spatial encoding by means of which the nuclear magnetic resonances can be assigned to positions or coordinates in the imaging volume. A further option is the use of a compartment model or compartment information to enable optimal k-space coverage of the first section during the performance of the second magnetic resonance measurement.

The extraction of the second magnetic resonance data from the first section of the dentition from the k-space data of the second magnetic resonance measurement can advantageously reduce the effort required for the reconstruction of second magnetic resonance images. Likewise, the extent of the k-space data acquired in the second magnetic resonance measurement can be advantageously reduced by using a local receiving antenna for acquiring nuclear magnetic resonances from the first section. This can advantageously reduce the effort and/or duration required for the reconstruction of the second magnetic resonance images.

According to a further aspect of the method according to the disclosure, the performance of the second magnetic resonance measurement takes place with a second imaging sequence, wherein the second imaging sequence is determined as a function of the abnormality of the first section. The second imaging sequence can, for example, be determined as a function of the abnormality of the first section, such as, for example, the positional information on the abnormality and/or the type of dental disease. In one example, the determination of the second imaging sequence includes an adaptation of the second imaging volume to the first section of the dentition. In a further example, the determination of the second imaging sequence includes increasing the spatial resolution of the second magnetic resonance measurement compared to the first magnetic resonance measurement. The second imaging sequence can differ from the first imaging sequence in at least one imaging parameter, such as, for example, the slice thickness, a dimension of the imaging volume, an echo time, a repetition time, a sampling density of the nuclear magnetic resonances or the like. Imaging sequences for the depiction of teeth can have very short echo times in order to a compensate a short T2 relaxation time of spins of the dentin or the enamel of the teeth and increase the contrast or signal intensity of the dentin or the enamel in the second magnetic resonance images. In one example, the echo time of the second magnetic resonance measurement is adapted as a function of dental caries in the first section in order to increase the sensitivity of the second magnetic resonance measurement in respect of the dentin of the at least one tooth in the first section. The second imaging sequence can furthermore be embodied to increase the contrast of inflammation, an injected anesthetic and/or prosthesis material.

The adaptation of the second imaging sequence as a function of the abnormality of the first section advantageously enables the second magnetic resonance measurement to be adapted to a diagnostically relevant issue. This can facilitate the quantitative and qualitative evaluation of the condition of the dentition and advantageously reduce the risk of a faulty evaluation.

In one possible aspect of the method according to the disclosure, first magnetic resonance images are compiled on the basis of the first magnetic resonance data and second magnetic resonance images are compiled on the basis of the second magnetic resonance data, wherein the first magnetic resonance images are registered with the second magnetic resonance images. The first magnetic resonance images and the second magnetic resonance images can be compiled by means of known image reconstruction methods. Registration of the first magnetic resonance images with the second magnetic resonance images can take place using any image registration methods desired. Examples of such image registration methods are area-based and/or feature-based methods based on a correlation function, correspondence of control points, global and/or local transformation, pattern recognition, a radial basis function, a Fourier transform or the like. The image registration methods can be further complemented by the use of optical and/or magnetic markers, the use of orientation points and/or a geometric equivalence of the positioning of the examination object relative to the magnetic resonance apparatus. Furthermore, the registration of the first magnetic resonance images and the second magnetic resonance images can take place on the basis of semi-rigid body models which, for example, only describe a relative movement between the lower jaw and the upper jaw.

It is conceivable for the first magnetic resonance images and the second magnetic resonance images or segments of the first magnetic resonance images and the second magnetic resonance images to be output together with the dental overview map. The dental overview map can further comprise representations of the number of teeth of the examination object and representations of abnormalities compiled as a function of the registered first magnetic resonance images and the second magnetic resonance images. Furthermore, the development of dental disease and/or a therapeutic measure can be determined on the basis of the registered magnetic resonance images and mapped by means of an indication, an identifier or a representation on a dental overview map.

The registration of the first magnetic resonance images with the second magnetic resonance images advantageously enables the progression of and/and or outcome of therapy for dental disease to be documented in the context of a longitudinal imaging study.

In one possible aspect, the method according to the disclosure includes a further step in which a deviation between the first magnetic resonance data and the second magnetic resonance data is determined, wherein information on the deviation is output together with the dental overview map. A deviation between the first magnetic resonance data and the second magnetic resonance data can, for example, be determined on the basis of a difference of values, such as, for example, contrast values or signal intensity values, a data space of the first magnetic resonance data and the second magnetic resonance data. Such values of the data space can, for example, be present in the form of tuples, vectors and/or matrices and be assignable to a position in an imaging volume. It is also conceivable for the determination of the deviation to take place on the basis of first magnetic resonance images and second magnetic resonance images reconstructed from the first magnetic resonance data and the second magnetic resonance data. Herein, the signal intensity or contrast of picture elements and/or volume elements of the first magnetic resonance images and the second magnetic resonance images can be correlated with one another in order to determine a deviation. The determination of the deviation between the first magnetic resonance images and the second magnetic resonance images preferably takes place by means of an image-processing unit.

It is conceivable for the dental overview map to be supplemented or expanded as a function of the deviation between the first magnetic resonance data and the second magnetic resonance data. This can mean that a representation of a tooth and/or an abnormality of the first section determined on the basis of the second magnetic resonance images is added to the dental overview map and/or superimposed thereon. An expansion of the dental overview map can, for example, include the addition of an indication providing information on the degree and/or progression of dental disease between the first time point and the second time point. It is in particular conceivable for a representation of a difference in an abnormality determined as a function of the deviation between the first magnetic resonance data and the second magnetic resonance data to be depicted on the dental overview map. Such a representation can, for example, include a schematized depiction of the difference in the volume, the area and/or the position of the abnormality between the first time point and the second time point. It is further conceivable for the representation of the difference in the abnormality to be depicted as a function of positional information on the abnormality to be depicted approximately in an anatomically correct relative position to the representation of the number of teeth in the dental overview map. Furthermore, the dental overview map can also comprise segments of the first magnetic resonance images and the second magnetic resonance images that are registered with one another, wherein a deviation between the segments of the first magnetic resonance images and the segments of the second magnetic resonance images is preferably highlighted in color.

In addition, any further deviations of the condition of the dentition between the first time point and the second time point can be marked or highlighted in the combined dental overview map. In particular absolute and/or relative information or units can be used in the documentation of the condition of the dentition by means of the dental overview map. For example, the indication can include a relative reduction of dental caries at a second time point compared to a first time point. The determination of the relative reduction of the dental caries preferably takes place by means of an image-processing unit which determines positional information on the abnormality at a first time point and a second time point and then ascertains the relative reduction. Obviously, spreading of dental disease from a first time point can be determined in a similar way at a second time point and output by means of the dental overview map. It is furthermore conceivable for the relative reduction or the relative spread to be indicated in relation to a reference value and/or a statistical range of normal values.

The determination of the deviation between the first magnetic resonance data and the second magnetic resonance data and the provision of the deviation by means of the dental overview map advantageously enables the development of dental disease and/or the effect of orthodontic treatment between the first time point and the second time point to be depicted and documented. This can advantageously reduce the effort required for diagnosis, the provision of results of the magnetic resonance measurement and/or the explanation of the result of a therapeutic measure to the examination object.

The magnetic resonance apparatus according to the disclosure includes a computing unit configured to coordinate a method according to the disclosure and carry it out by means of the magnetic resonance apparatus. For the acquisition, processing and storage of data, such as, for example, the first magnetic resonance data, the second magnetic resonance data, the first magnetic resonance images, the second magnetic resonance images and the dental overview map, in addition to the computing unit, the magnetic resonance apparatus can comprise a control unit, a working memory, a data storage device and a suitable interface for inputting and outputting data. The computing unit can, for example, include a controller, a microcontroller, a CPU, a GPU or the like. The working memory and the data memories comprise storage technologies such as RAM, ROM, PROM, EPROM, EEPROM, flash memories, HDD storage devices, SSD storage devices or the like. It is conceivable for the data storage device to be an internal storage unit electrically and/or mechanically connected to the computing unit of the magnetic resonance apparatus. However, it is also conceivable for the data storage device to be an external storage unit connected to the computing unit by means of a network connection. Examples of external storage units are network servers with corresponding data storage devices and cloud storage. The data can be transmitted by means of analog and/or digital signals and suitable electrical or wireless signal connections between the components of the magnetic resonance apparatus.

The computing unit is preferably electrically connected to a control unit of the magnetic resonance apparatus and/or integrated in the control unit. The control unit can be configured to perform a method according to the disclosure under the coordination of the computing unit. The control unit can, for example, be embodied to perform a magnetic resonance measurement of the examination object, acquire magnetic resonance data from the examination object and transmit the magnetic resonance data to other components, such as, for example, the computing unit and/or the storage unit. The computing unit can be configured to read in the magnetic resonance data and compile magnetic resonance images on the basis of the magnetic resonance data. Furthermore, the computing unit can be configured to perform an analysis of sections of the examination object's dentition. The computing unit preferably comprises an image-processing unit configured to determine an abnormality of a first section and positional information on the abnormality. Further, the computing unit and/or the image-processing unit can be embodied to compile a dental overview map of an examination object as a function of magnetic resonance data and/or magnetic resonance images of the examination object and transmit them to the storage unit. The computing unit can transmit the dental overview map and/or the magnetic resonance images of the examination object to a display unit and/or a mobile device by means of an output interface.

The components of the magnetic resonance apparatus according to the disclosure can be matched to one another such that a time-efficient robust performance of a method according to the disclosure is enabled. In particular, the method according to the disclosure or partial steps of the method according to the disclosure can take place automatically such that the coordination of individual method steps takes place as autonomously as possible. Hence, the performance of a method according to the disclosure does not require any specialist knowledge and can be initiated by any member of the medical staff.

The computer program product according to the disclosure can be loaded into in a data storage device of a computing unit of the magnetic resonance apparatus and comprises program code means for carrying out a method according to the disclosure when the computer program product is executed in the computing unit of the magnetic resonance apparatus. The computer program product according to the disclosure enables the method according to the disclosure to be carried out in a quick, identically repeatable and robust manner. The computer program product is configured such that it can carry out the method steps according to the disclosure by means of the computing unit. Herein, the computing unit must in each case fulfill the requisite conditions such as, for example, an appropriate working memory, an appropriate graphics card or an appropriate logic unit so that the respective method steps can be carried out efficiently. The computer program product is, for example, held on a computer-readable medium or on a network, a server or a cloud from where it can be loaded into processor of a local computing unit. Herein, the computing unit can be embodied as an independent system component or as a part of the magnetic resonance apparatus. Furthermore, control information of the computer program product can be stored on an electronically readable data carrier. The control information of the electronically readable data carrier can also be embodied to carry out a method according to the disclosure when the data carrier is used in the computing unit of the magnetic resonance apparatus. Examples of electronically readable data carriers are a DVD, a magnetic tape, a USB stick or any other data storage device on which electronically readable control information, in particular software, is stored. When this control information is read from the data carrier and transmitted to a control unit and/or the computing unit of the magnetic resonance apparatus, all the aspects according to the disclosure of the described method according to the disclosure can be performed.

BRIEF DESCRIPTION OF THE DRAWINGS

Further advantages and details of the present disclosure may be derived from the exemplary aspects described in the following and with reference to the drawings, in which:

FIG. 3 shows a schematic depiction of a dental overview map according to a second aspect of the method according to the disclosure, FIG. 4 shows a schematic depiction of a dental overview map according to a third aspect of the method according to the disclosure.

The following description of the figures refers to a human patient as an examination object since this is a conventional application for an imaging examination. Obviously, this does not exclude the application of the method according to the disclosure to other examination objects.

DETAILED DESCRIPTION

Figure 1:
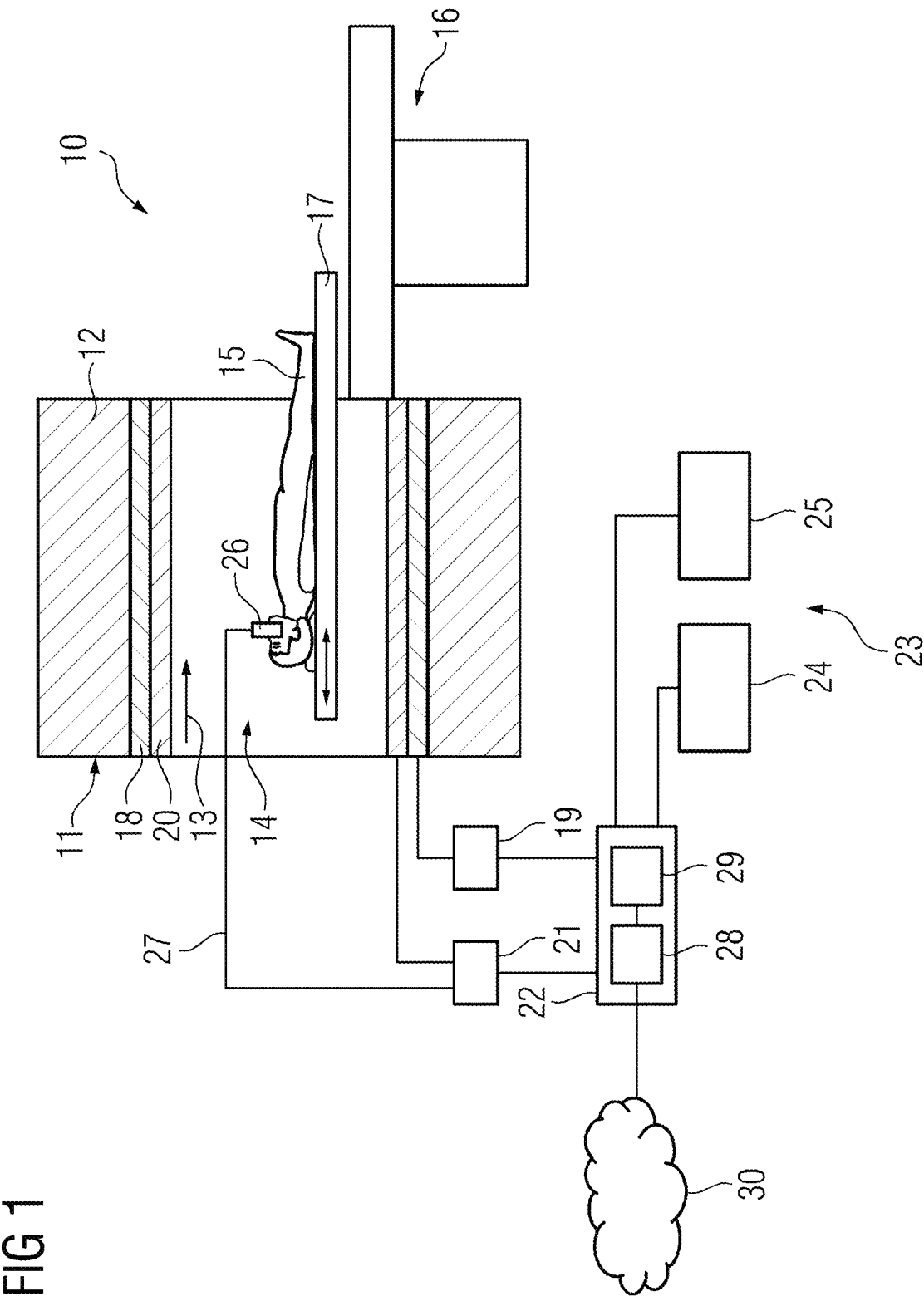
FIG. 1 shows an aspect of a magnetic resonance apparatus according to the disclosure.

FIG. 1 depicts a possible aspect of the magnetic resonance apparatus 10 according to the disclosure. The magnetic resonance apparatus 10 includes a magnet unit 11 comprising, for example, a permanent magnet, an electromagnet or a superconducting main magnet 12 for generating a strong and in particular homogeneous main magnetic field 13. The magnetic resonance apparatus 10 also includes a patient-receiving region 14 for receiving a patient. In the present exemplary aspect, the patient-receiving region 14 is cylindrical and surrounded by the magnet unit 11 in a circumferential direction. However, in principle, aspects of the patient-receiving region 14 that differ from this example are also conceivable.

The patient can be positioned in the patient-receiving region 14 by means of a patient support apparatus 16 of the magnetic resonance apparatus 10. For this purpose, the patient support apparatus 16 comprises a patient table 17 that can be moved within the patient-receiving region 14. The magnet unit 11 furthermore comprises a gradient coil 18 for generating magnetic gradient fields used for spatial encoding during imaging. The gradient coil 18 is actuated by means of a gradient control unit 19 of the magnetic resonance apparatus 10. The magnet unit 11 can furthermore include a radio-frequency antenna embodied in the present exemplary aspect as a body coil 20 permanently integrated in the magnetic resonance apparatus 10. The body coil 20 is designed to excite nuclear spins located in the main magnetic field 13 generated by the main magnet 12. The body coil 20 is actuated by a radio-frequency unit 21 of the magnetic resonance apparatus 10 and radiates radio-frequency excitation pulses into an image-recording region substantially formed by a patient-receiving region 14 of the magnetic resonance apparatus 10. The body coil 20 is furthermore embodied to receive nuclear magnetic resonances.

To control the main magnet 12, the gradient control unit 19 and to control the radio-frequency unit 21 the magnetic resonance apparatus 10 comprises a control unit 22. The control unit 22 is embodied to control the performance of a sequence, such as, for example, an imaging GRE (gradient echo) sequence, a TSE (turbo spin echo) sequence or a UTE (ultra-short echo time) sequence. The control unit 22 also includes a computing unit 28 for evaluating magnetic resonance data acquired during a magnetic resonance measurement. The computing unit 28 of the magnetic resonance apparatus 10 can be embodied to use reconstruction methods in order to reconstruct magnetic resonance images on the basis of the magnetic resonance data. Further, the computing unit can be embodied to compile a dental overview map 40 (40a, 40b, 40c) as a function of the magnetic resonance data. In the present example, the computing unit 28 is connected to a storage unit 29 and a cloud storage 30. The computing unit can be configured to store data such as, for example, magnetic resonance images, magnetic resonance data and/or dental overview maps 40 on the storage unit 29 and the cloud storage 30 and retrieve this data from this storage unit or the cloud storage by means of a suitable interface. It is also conceivable, by means of a suitable application, for the patient 15 to use a mobile device (not shown) to access a storage region containing magnetic resonance images and/or dental overview maps of the patient 15. Accordingly, the software application can be configured to output the magnetic resonance images and/or the dental overview map 40 on a screen of the mobile device.

The magnetic resonance apparatus 10 also includes a user interface 23 with a signal connection to the control unit 22. Control information, such as, for example, imaging parameters, but also reconstructed magnetic resonance images and/or dental overview maps 40, can be displayed on a display unit 24, for example, on at least one monitor, of the user interface 23 for a user. Furthermore, the user interface 23 comprises an input unit 25 by means of which parameters of a magnetic resonance measurement can be input by the user.

The magnetic resonance apparatus 10 can further comprise a local receiving antenna 26 positioned on the dentition of a patient 15 which acquires nuclear magnetic resonances of a tooth or a plurality of teeth of the patient 15 and transmits them to the computing unit 28 of the control unit 22. The local receiving antenna 26 preferably comprises an electrical connecting lead 27 providing a signal connection to the radio-frequency unit 21 and the control unit 22. Like the body coil 20, the local receiving antenna 26 can also be embodied to excite nuclear spins and receive nuclear magnetic resonances. For this purpose, the local receiving antenna 26 can in particular have a drum-shaped structure enclosing the head of the patient 15. To emit radio-frequency excitation pulses, the local receiving antenna 26 is actuated by the radio-frequency unit 21.

The magnetic resonance apparatus 10 depicted can obviously include further components usually comprised by magnetic resonance apparatuses. It is also conceivable, instead of a cylindrical structure, for the magnetic resonance apparatus 10 to have a C-shaped, triangular or asymmetrical structure of the magnetic-field-generating components. The magnetic resonance apparatus 10 can in particular be embodied to perform a magnetic resonance examination of a standing or seated patient 15. It is further conceivable for the magnetic resonance apparatus 10 to be specially embodied to perform imaging examinations of the dentition of a patient 15.

Figure 2:
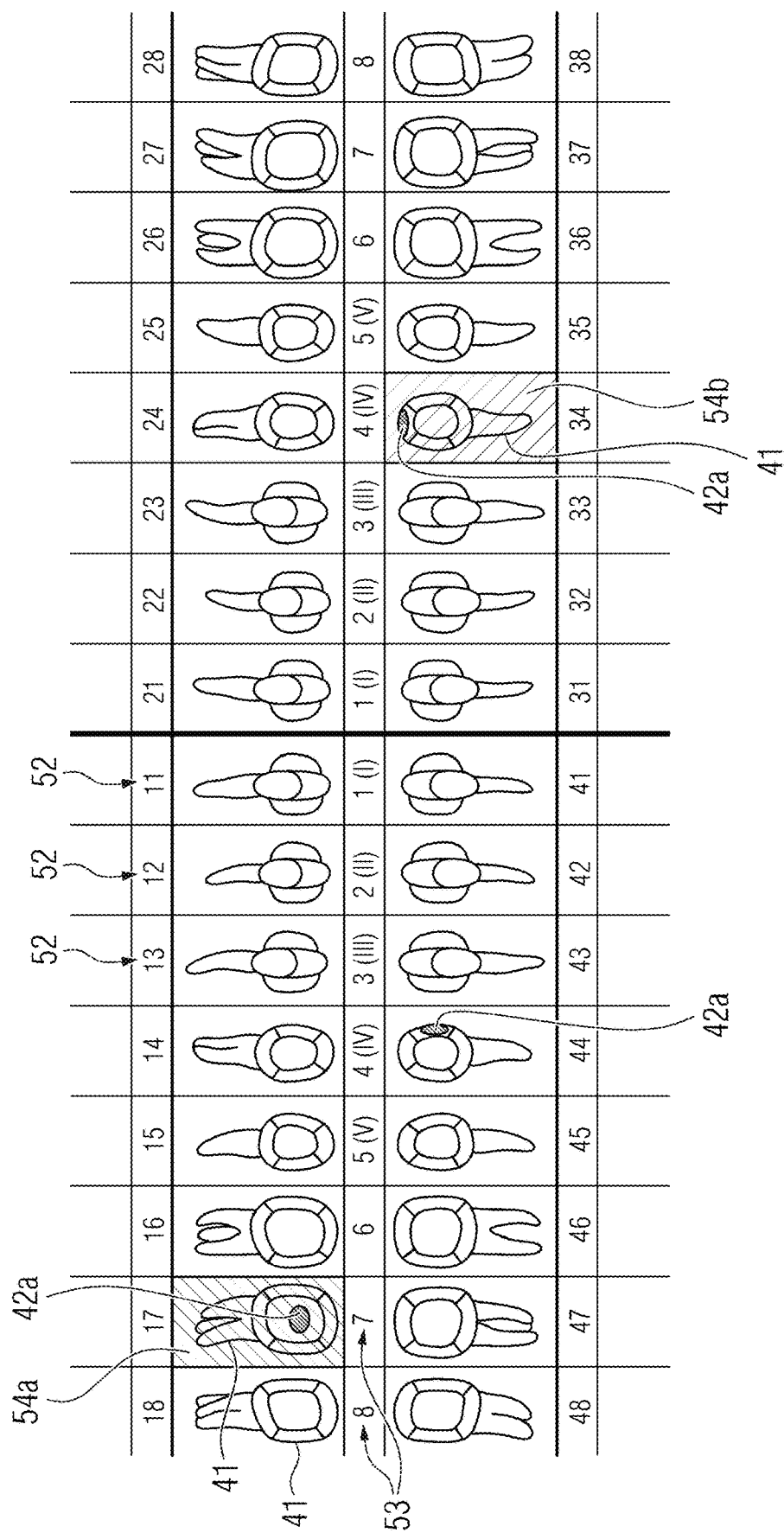
FIG. 2 shows a schematic depiction of a dental overview map according to a first aspect of the method according to the disclosure.

FIG. 2 shows a schematic depiction of a dental overview map 40. The dental overview map 40 includes a structured depiction of the number of teeth of the patient 15. Herein, individual teeth of the patient 15 are depicted as representations of a tooth 41. Herein, the representations of the teeth 41 are arranged such that a type of a tooth can be identified on the basis of the schematized depiction of the representation of the tooth 41. The dental overview map 40 further contains numbering 52 assigning a unique identification number to each tooth of the number of teeth in the patient's dentition. In the present example, the teeth on the left side and the right side of the upper jaw and of the lower jaw are numbered consecutively in each case starting with an anterior incisor. The dental overview map 40 further comprises identifications 53 identifying a respective position of a tooth along the dental arches. Obviously, in addition to the method shown for numbering and/or identifying the teeth, any other method is also conceivable.

The dental overview map 40 further comprises a marking 54a indicating inflammation of the tooth numbered "17" at the seventh position on the left side of the upper jaw. In the example shown, the marking 54a is shown as a frame enclosing the tooth numbered "17". On the other hand, the tooth numbered "34" at the fourth position of the right lower jaw has dental caries, for example. Herein, the representation of the dental caries 42a is positioned on the representation of the tooth 41 such that a relative position between the representation of the tooth 41 and the representation of the dental caries 42b approximately matches an anatomically correct relative position between the dental caries and the tooth in question. Herein, the shape and/or dimension of the representation of the dental caries 42a can be correlated with a shape and/or a dimension of the dental caries. In the example shown, the tooth numbered "34" additionally has a marking 54b which has a different color from the marking 54a and indicates the presence of inflammation. On the other hand, the tooth numbered "44" only has a representation of dental caries 42a. Therefore, any additional inflammation of the tooth can be excluded in the case of this tooth.

FIG. 3 shows a simplified form of depiction of the dental overview map 40. In the present example, the dental overview map 40a was compiled on the basis of first magnetic resonance data from a first magnetic resonance measurement. With this form of depiction, the teeth 41 are represented by means of simple boxes which are arranged in two rows representing the two dental arches of the dentition of the patient 15. The dental overview map 40a has markings 54a and 54b indicating the presence of different dental diseases. In the present example, the marking 54a indicates inflammation of the tooth while the marking 54b indicates dental caries. Herein, the markings 54a and 54b can differ, for example, in a color, a gray level and/or a pattern in order to indicate different dental diseases. The representations of teeth 41 with the markings 54a and 54b have further indications 51 encoding a degree and/or a state of progression of the dental disease present in each case. In the example shown, the severity of the dental disease increases on a scale of "1" to "10". The number "1" can mean, for example, that the dental disease on the tooth in question is still in an initial stage. On the other hand, the number "4" can mean that the dental disease is already at an advanced stage.

FIG. 4 shows a second dental overview map 40b compiled. For example, on the basis of the second magnetic resonance measurement or on the basis of measurement data from subsequent imaging examinations. In order to reduce the duration of the second magnetic resonance measurement, the second imaging region of the second magnetic resonance measurement was reduced to sections found to have an abnormality during the analysis of the first magnetic resonance data. In the present example, the progression and/or degree of the dental disease is encoded by means of a color or a gray level of the markings 54a and 54b. Herein, different dental diseases can, for example, be distinguished on the basis of different patterns or colors of the markings 54a and 54b. This simplified form of depiction of the second dental overview map 40b is in particular suitable for transmitting to a mobile device and informing the patient 15 of the condition of the dentition.

Figure 5:
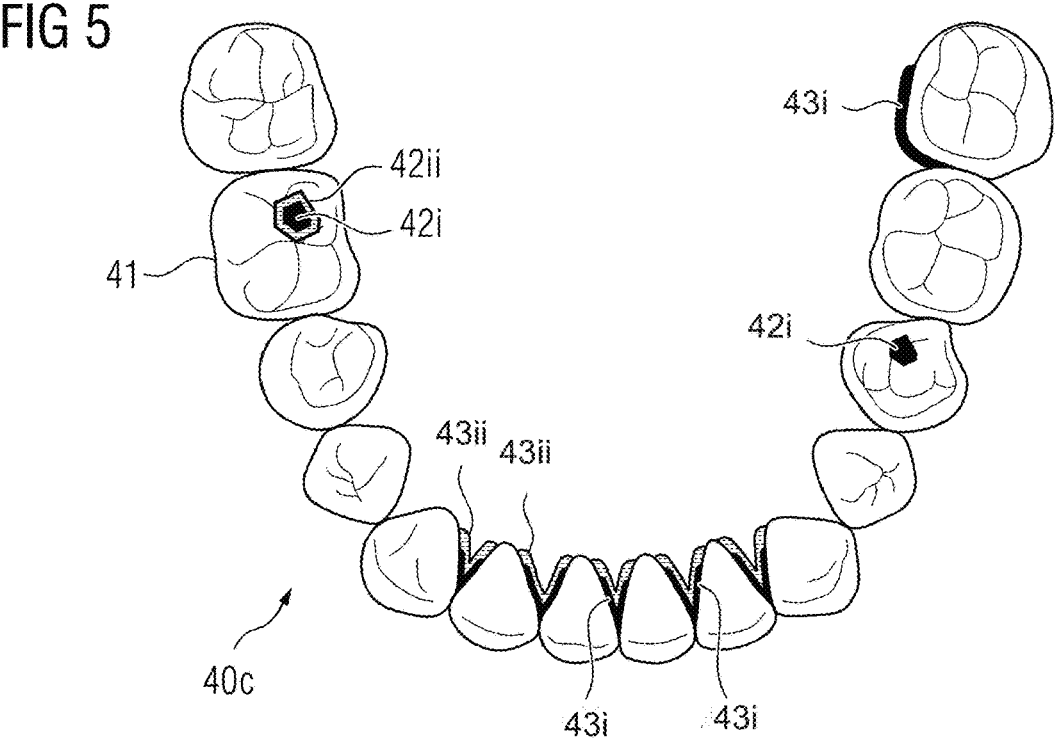
FIG. 5 shows a schematic depiction of a dental overview map according to a fourth aspect of the method according to the disclosure.

FIG. 5 shows a schematized depiction of a combined dental overview map 40c compiled as a function of the first magnetic resonance data and the second magnetic resonance data (and/or further measurement data from imaging examinations). In the example depicted, the combined dental overview map 40c includes representations of the teeth 41 of the lower jaw of the patient 15. Preferably, during the compilation of the combined dental overview map 40c, the abnormalities of sections of the dentition determined on the basis of the second magnetic resonance data are superimposed on a first dental overview map 40a with a comparable form of depiction such that a progression and/or a development of dental disease between the first time point and the second time point can be quantified on the basis of the combined dental overview map 40c. For example, a molar of the patient 15 has dental caries which has spread between the first time point and the second time point. The spread of the dental caries is visually highlighted by means of the larger dimension of the representation of the dental caries 42ii determined at the second time point compared to the representation of the dental caries 42i determined at the first time point. In the present example, the spread of the dental caries to further teeth of the lower jaw between the first time point and the second time point has remained constant and therefore superimposition with the representation of the dental caries 42ii in the second dental overview map is not necessary.

In a second example, incisors of the lower jaw of the patient 15 have periodontitis in a transitional region to the gingival tissue. The degree of the inflamed gum tissue determined on the basis of the first magnetic resonance data is depicted by means of the representation of the periodontitis 43 i in the combined dental overview map 40 c. Since, as the result of a corresponding therapeutic measure, the inflammation of the gum tissue has reduced between the first time point and the second time point, the region identified by means of the representation of the periodontitis 43 ii has a smaller area than the region identified by means of the representation 43 i.

A dental overview map 40 shown in FIGS. 3, 4 and 5 is preferably compiled on the basis of magnetic resonance data from a magnetic resonance apparatus 10. It is, however, conceivable for a method according to the disclosure described above to be transferred to other imaging methods. It is also conceivable for existing data sets from other imaging methods to be used to compile and/or supplement a dental overview map 40 without performing another imaging examination. As described above, possible imaging methods could, for example, be X-ray methods or intraoral camera methods.

Figure 6:
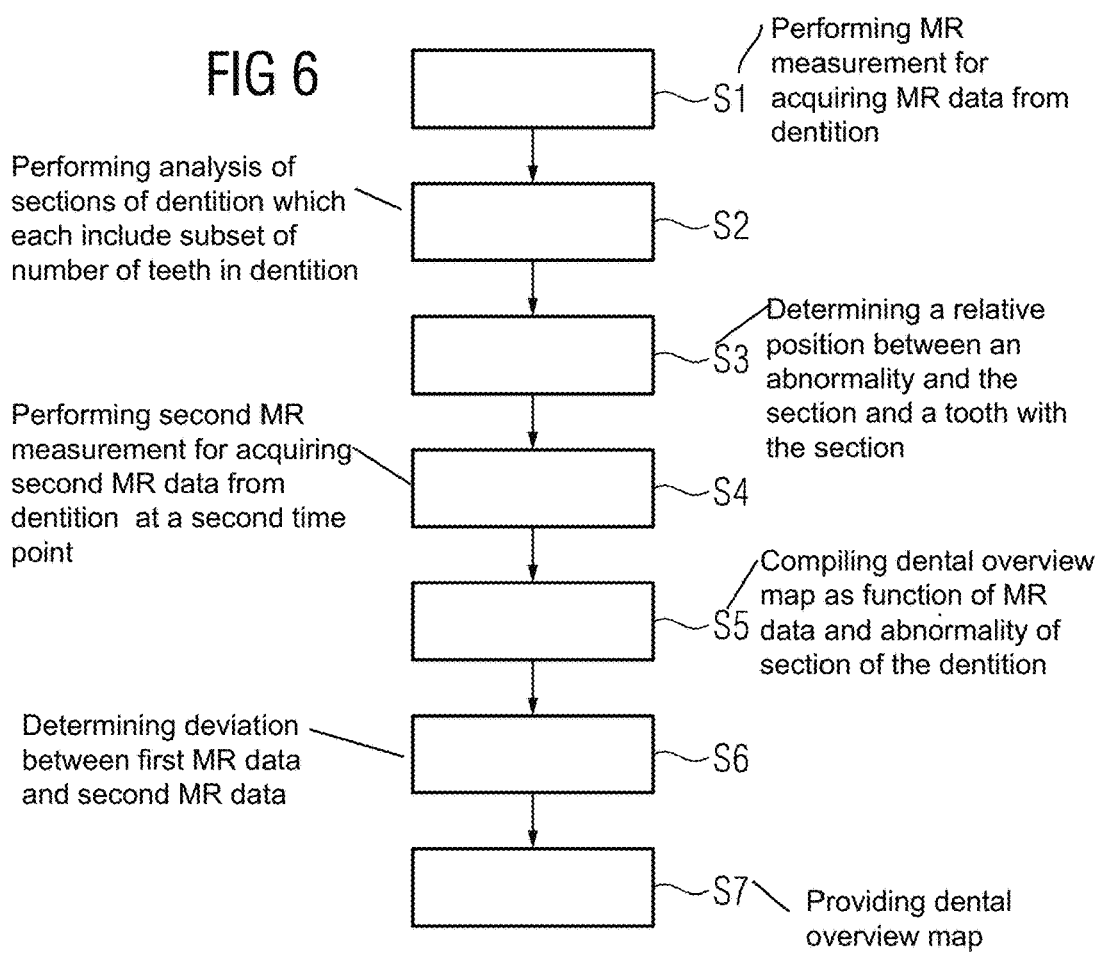
FIG. 6 shows a possible flow chart according to an aspect of the method according to the disclosure.

FIG. 6 shows a possible flow chart of a method according to the disclosure for compiling a dental overview map 40 of the dentition of a patient 15 on the basis of magnetic resonance data from a magnetic resonance measurement of the dentition.

In a step S1 of the method according to the disclosure, a magnetic resonance measurement for acquiring magnetic resonance data from the dentition is performed, wherein an imaging volume of the magnetic resonance measurement is matched with a volume of the dentition and wherein the imaging volume includes a number of teeth in the dentition. For this purpose, the patient 15 is initially positioned in a patient-receiving region 14 such that a diagnostically relevant region of the dentition matches the imaging region of the magnetic resonance apparatus 10. The patient 15 is preferably positioned by means of a patient support apparatus 16 for transporting the patient 15 into the cylindrical patient-receiving region 14 of a conventional radiological magnetic resonance apparatus 10. However, it is also conceivable for the magnetic resonance apparatus 10 to be a dedicated imaging apparatus for recording magnetic resonance data from a dental region of the patient 15 with which the patient-receiving region 14 can be adapted to a head of the patient 15 in any way desired. It is, for example, conceivable for the magnetic resonance apparatus 10 to be positioned along a mechanical guide in relation to the head of the patient 15 until the imaging volume matches the diagnostically relevant region of the dentition. Herein, the diagnostically relevant region includes a number of teeth, from which magnetic resonance data is to be acquired in the context of an evaluation of the condition of the dentition. The diagnostically relevant region can, for example, be established in advance of the magnetic resonance measurement by the attending medical practitioner. The magnetic resonance measurement can be performed as described above.

In one aspect, multiple magnetic resonance measurements of the dentition of the patient 15 are performed in the context of a longitudinal imaging study of the patient 15. Here, the step (S1) includes the performance of a first magnetic resonance measurement for acquiring first magnetic resonance data from the dentition at a first time point, wherein a first imaging volume of the first magnetic resonance measurement is matched with a first volume of the dentition and includes a first number of teeth.

In a further step S2, an analysis of sections of the dentition each of which include a subset of the number of teeth in the dentition is performed in order to determine an abnormality on the basis of the magnetic resonance data, wherein an abnormality is determined in at least one section. For this purpose, the magnetic resonance data is divided into sections, wherein a section preferably includes magnetic resonance data from exactly one tooth of the number of teeth. It is also conceivable for the analysis of the sections of the dentition to take place on the basis of magnetic resonance images which are reconstructed from the magnetic resonance data. Herein, a section can, for example, be a segment of a magnetic resonance image which includes exactly one tooth of the number of teeth. Herein, the analysis of the sections takes place section-by-section, i.e. for each individual section, until all the sections of the magnetic resonance data and/or magnetic resonance images have been analyzed. The sections are preferably analyzed by means of a suitable image-processing unit which in each case analyzes exactly one section or a plurality of sections in parallel as the function of the configuration of a processor of the image-processing unit. The analysis can, for example, include the correlation of contrasts or signal intensities of picture elements and/or volume elements of the magnetic resonance images with a reference value from a database and/or a normal value of the magnetic resonance images. The reference value can, for example, be a typical dental caries contrast in a magnetic resonance image with a given imaging sequence. It is also conceivable for characteristic structures to be derived from the contrasts or signal intensities of a plurality of picture elements, wherein said characteristic structures can be assigned to an anatomical structure and/or an abnormality. For example, a hole in a tooth can be identified on the basis of a different contrast from the dental enamel or dentin of the tooth by means of the image-processing unit and distinguished from an intact part of the tooth in question.

In one aspect, the at least one section in which an abnormality is established is a first section, wherein, during the performance of the analysis of sections of the dentition, a presence of an abnormality in a second section is excluded. This can mean that an abnormality is determined in at least one tooth in the dentition while abnormalities on further teeth are excluded. However, it can also mean that an abnormality is excluded in at least one tooth in the dentition while the further teeth in the dentition have an abnormality. Obviously, the number of teeth can have a plurality of sections with an abnormality and a plurality of sections without abnormalities as long as at least one section with an abnormality is determined and one section has no abnormality.

In a further aspect, the performance of the analysis of sections of the dentition includes the determination of inflammation and/or dental caries. Preferably, the inflammation and/or the dental caries is determined during the analysis of the sections of the dentition as a function of the contrast or signal intensity of the magnetic resonance data and/or the magnetic resonance images. For this, the magnetic resonance measurement can be performed with an imaging sequence which provides a high soft-tissue contrast. An example of such an imaging sequence is a SE (spin echo) or a GRE (gradient echo) sequence with high echo times. However, in particular in the case of the suspicion of dental caries with hole formation, it is also possible to use an imaging sequence which maps the dentin and/or the dental enamel with a high signal intensity. Possible imaging sequences can, for example, have very short echo times in order to compensate a short T2 relaxation time of spins of the dentin or of the enamel. Very short echo times can, for example, be below 150 µs or below 70 µs. Examples of possible imaging sequences are FLASH (fast low-angle shot) or UTE (ultra-short echo time) sequences.

In an optional step S3, a relative position between an abnormality of the at least one section and at least one tooth with the at least one section is determined. The determination of the relative position between the abnormality of the at least one section and the at least one tooth preferably takes place on the basis of contrasts or signal intensities of the magnetic resonance data and/or the magnetic resonance image of the at least one tooth. For example, contrasts of one or more picture elements can have a characteristic structure and/or an abnormal deviation of the signal intensity compared to surrounding and/or adjacent picture elements. In particular, when using a UTE sequence, the contour of the at least one tooth can be determined on the basis of a characteristic distribution of signal-intensive picture elements while the contour of dental disease can be distinguished from the at least one tooth due to abnormally low signal intensities, for example. In other words, a circumferential contour of the dental disease can be determined on the basis of contrast differences to the at least one tooth. Finally, items of positional information, such as, for example, the coordinates of points on the circumferential contours of the at least one tooth and the dental disease can be correlated with one another in order to determine the relative position between the at least one tooth and the dental disease.

In an optional step S4, a second magnetic resonance measurement for acquiring second magnetic resonance data from the dentition of the patient 15 is performed at a second time point, wherein a second imaging volume of the second magnetic resonance measurement is matched with a second volume of the dentition and includes at least one tooth and wherein at least one imaging parameter of the second magnetic resonance measurement is determined as a function of the abnormality of the first section. As described above, the second time point is later than the first time point. Preferably, at least one imaging parameter of the second magnetic resonance measurement is changed compared to the first magnetic resonance measurement in order to adapt the second imaging volume to the volume of the dentition with the first section. This can mean that only magnetic resonance data from sections with abnormalities is acquired during the second magnetic resonance measurement. As FIG. 4 shows, the second imaging volume of the second magnetic resonance measurement can, for example, be restricted to six teeth in the dentition of the patient 15 in order to quantify the development of the dental caries and the inflammation which were determined during the analysis of the sections of the dentition on the basis of the first magnetic resonance data. Herein, the second imaging volume can be restricted as a function of the relative position of the teeth in question to a single tooth, individual groups of teeth or all of the six teeth in order to acquire these teeth with a higher recording quality. For this, it is in particular conceivable for a plurality of imaging sequences to be performed with different second imaging volumes which are each matched to a volume of the dentition with the single tooth or the group of teeth. Herein, at least one imaging parameter of the second magnetic resonance measurement is determined as a function of the abnormality of the first section. Based on the example in FIG. 4, this can mean that the second magnetic resonance data from the sections with the teeth affected by inflammation of the gum tissue are recorded with a second imaging sequence that provides high soft-tissue contrast. On the other hand, in the sections with teeth affected by dental caries, an echo time of the second magnetic resonance measurement is changed compared to the first magnetic resonance measurement in order to increase the contrast of the dentin or the enamel of the affected teeth.

In one aspect, the performance of the second magnetic resonance measurement for acquiring second magnetic resonance data from the first section takes place with a second recording quality, wherein the second recording quality is higher than or equal to the first recording quality used during the performance of the first magnetic resonance measurement for the acquisition of the first magnetic resonance data from the first section. Preferably, the recording of second magnetic resonance data from teeth in which dental disease was determined during the analysis of the sections of the dentition on the basis of the first magnetic resonance data takes place with higher spatial resolution. The spatial resolution of the second magnetic resonance measurement can, for example, be increased by reducing the slice thickness. Preferably, herein the spatial resolution is increased selectively in teeth with dental disease.

In a further aspect, the performance of the second magnetic resonance measurement acquiring second magnetic resonance data from the second section takes place with a third recording quality, wherein the third recording quality is lower than the first recording quality used during the performance of the first magnetic resonance measurement for the acquisition of the first magnetic resonance data from the first section. This can mean that the recording of second magnetic resonance data from teeth without abnormalities takes place with lower spatial resolution. For example, the spatial resolution of such sections during the performance of the second magnetic resonance measurement can be so low that exact quantification of the degree of dental disease is inexpedient. However, the spatial resolution can be sufficient to enable the presence of dental disease to be reliably determined by means of an analysis of the sections of the second magnetic resonance data.

In one possible aspect, the performance of the second magnetic resonance measurement for the acquisition of second magnetic resonance data from the first section takes place with a second recording quality and the performance of the second magnetic resonance measurement for the acquisition of second magnetic resonance data from the second section takes place with a third recording quality, wherein the second recording quality is higher than the third recording quality. Preferably, with this aspect, the second magnetic resonance measurement comprises a plurality of imaging sequences. Herein, during one imaging sequence of the plurality of imaging sequences, in each case second magnetic resonance data can be acquired from exactly one tooth or a plurality of teeth with an abnormality that are adjacent to one another and/or positioned on above the other. Herein, the imaging sequences can have different imaging volumes adapted to the exactly one tooth or the plurality of teeth positioned next to one another and/or on above the other. Herein, the spatial resolution of teeth with an abnormality is increased compared to teeth without abnormalities by adapting the slice thickness, for example.

In a further aspect, first magnetic resonance images are compiled on the basis of the first magnetic resonance data and second magnetic resonance images are compiled on the basis of the second magnetic resonance data, wherein the first magnetic resonance images are registered with the second magnetic resonance images. The registration of the first magnetic resonance images and the second magnetic resonance images takes place, for example, by means of rigid or elastic image registration methods. Preferably, the combined dental overview map 40*c* is compiled on the basis of the registered first magnetic resonance images and second magnetic resonance images. Herein, segments of the registered magnetic resonance images, such as, for example, magnetic resonance images of individual teeth, can be output together with the combined dental overview map 40*c*.

In a further step S5, a dental overview map 40 is compiled as a function of the magnetic resonance data and the abnormality of the section of the dentition, wherein the dental overview map 40 comprises a representation of the number of teeth 41 of the dentition of the patient 15 and a representation of the abnormality 42 of the section of the dentition. It is conceivable for the number of teeth to be analyzed on the basis of contrasts or signal intensities of the magnetic resonance data in order to identify the type of each tooth of the number of teeth. For each tooth type identified, it is, for example, possible to read in a corresponding representation from a storage unit 29 or a cloud storage 30 and use it for the compilation of the dental overview map 40. However, it is also conceivable for the dental overview map 40 to be compiled on the basis of reconstructed magnetic resonance images of the magnetic resonance measurement. The magnetic resonance images enable, for example, a shape and/or an outline contour of the teeth to be derived and used as a representation. The representations of the teeth 41 are preferably structured during the compilation of the dental overview map 40, i.e. depicted corresponding to an anatomically correct arrangement of the teeth. Furthermore, the teeth can be provided with numbering 52 and/or an identifier 53 which, for example, include information on a type and/or a position of a tooth in the dentition of the patient 15. Likewise, the representation of the abnormality 42 can be compiled on the basis of an identified shape and/or an identified outline contour or read from a data storage device. As shown in FIGS. 2 to 5, it is conceivable for the representation of the abnormality 42 to comprise markings 54 and/or indications 51 providing information on the type, position and/or degree of dental disease.

In one possible aspect, the compilation of the dental overview map 40 takes place as a function of the relative position between the abnormality of a section and the at least one tooth of the section. As shown in FIG. 5, during the compilation of the combined dental overview map 40c, the representation of dental disease 42 is positioned relative to the representation of the tooth 41 such that the position of the representation of the dental disease 42d at least approximately matches an anatomically correct position of the dental disease on the tooth.

In an optional step S6, a deviation between the first magnetic resonance data and the second magnetic resonance data is determined, wherein information on the deviation is output together with the dental overview map 40. The determination of the deviation in particular takes place on the basis of a difference of contrast values or signal intensity values of the first magnetic resonance data and the second magnetic resonance data. It is however also conceivable for the determination of the deviation to take place on the basis of contrasts of picture elements of first magnetic resonance images and second magnetic resonance images which are reconstructed from the first magnetic resonance data and second magnetic resonance data. The determination of the deviation can, for example, include the correlation of positional information on a tooth or an abnormality. The deviation of the positional information between the first time point and the second time point can be used as the basis for deriving the development of dental disease or a tooth position depicted, for example, in the form of an indication 51, a marking 54 and/or a representation of the abnormality 42 on the combined dental overview map 40c. As shown in FIG. 5, a representation of the dental caries 42a at the first time point can be superimposed by a representation of the dental caries 42b at the second time point in order to depict the development of the dental disease.

In a further step S7 of the method, the dental overview map 40 is provided. It is conceivable for the dental overview map 40 to be transmitted to a storage unit 29 and/or a cloud storage 30 during the provision. It is also conceivable for the dental overview map 40 to be transmitted to a display unit 24 of the magnetic resonance apparatus 10 in the context of an evaluation of the condition of the dentition of the patient 15. The dental overview map 40 can further be output to a display unit or a computing unit of a mobile device of the patient 15. The computing unit of the mobile device can be configured to process the dental overview map 40 by means of a dedicated software application, for example to improve teeth cleaning of the dentition. Herein, the provision of the dental overview map 40 to the display unit 24, the storage unit 29, the cloud storage 30 and/or the mobile device of the patient 15 can take place in a wired or wireless manner by means of suitable interfaces.

Of course, the aspects of the method according to the disclosure and the ultrasound recording apparatus should be understood as being exemplary. Therefore, individual aspects can be expanded with features of other aspects. In particular, the sequence of the method steps of the method according to the disclosure should be understood as being by way of example. The individual steps can also be performed in another sequence or partially or completely overlap in time.

The invention claimed is:

1. A method for compiling a dental overview map of a dentition of an examination object on the basis of magnetic resonance (MR) data from a magnetic resonance measurement of the dentition, comprising:
performing an MR measurement for acquiring MR data from the dentition, wherein an imaging volume of the MR measurement is matched with a volume of the dentition, and the imaging volume includes a number of teeth in the dentition; and
performing an analysis of sections of the dentition, each of which includes a subset of the number of teeth in the dentition in order to determine an abnormality on the basis of the MR data, wherein an abnormality is determined in at least one section,
wherein the MR measurement is a first MR measurement, the first MR measurement for acquiring first MR data from the dentition is performed at a first time point, a first imaging volume of the first MR measurement is matched with a first volume of the dentition and includes a first number of teeth, and the at least one section in which the abnormality is determined is a first section,
wherein in one step, a second MR measurement for acquiring second MR data from the dentition is performed at a second time point, wherein a second imaging volume of the second MR measurement with a second volume of the dentition and includes at least one tooth and wherein at least one imaging parameter of the second MR measurement is determined as a function of the abnormality of the first section, and
wherein the performance of the second MR measurement for acquiring second MR data from the second section takes place with a third recording quality, and the third recording quality is lower than a first recording quality used during the performance of the first MR measurement for the acquisition of the first MR data from the first section.

2. The method as claimed in claim 1, wherein the at least one section in which the abnormality is determined is a first section, and during the performance of the analysis of sections of the dentition, a presence of an abnormality in a second section is excluded.

3. The method as claimed in claim 1, wherein the performance of the analysis of sections of the dentition includes a determination of inflammation or dental caries.

4. The method as claimed in claim 1, further comprising:
determining a relative position between an abnormality of the at least one section and at least one tooth with the at least one section,
wherein the compilation of the dental overview map takes place as a function of the relative position between the abnormality of the at least one section and the at least one tooth.

5. The method as claimed in claim 1, further comprising:
compiling a dental overview map as a function of the MR data and the abnormality of the at least one section of the dentition, wherein the dental overview map comprises a representation of a tooth of the examination object's dentition and a representation of the abnormality of the at least one section of the dentition; and
providing the dental overview map.

6. A method for compiling a dental overview map of a dentition of an examination object on the basis of magnetic resonance (MR) data from a magnetic resonance measurement of the dentition, comprising:
performing an MR measurement for acquiring MR data from the dentition, wherein an imaging volume of the MR measurement is matched with a volume of the dentition, and the imaging volume includes a number of teeth in the dentition; and performing an analysis of sections of the dentition, each of which includes a subset of the number of teeth in the dentition in order to determine an abnormality on the basis of the MR data, wherein an abnormality is determined in at least one section, wherein the MR measurement is a first MR measurement, the first MR measurement for acquiring first MR data from the dentition is performed at a first time point, a first imaging volume of the first MR measurement is matched with a first volume of the dentition and includes a first number of teeth, and the at least one section in which the abnormality is determined is a first section, wherein in one step, a second MR measurement for acquiring second MR data from the dentition is performed at a second time point, wherein a second imaging volume of the second MR measurement with a second volume of the dentition and includes at least one tooth and wherein at least one imaging parameter of the second MR measurement is determined as a function of the abnormality of the first section, and wherein the performance of the second MR measurement for the acquisition of second MR data from the first section takes place with a second recording quality and the performance of the second MR measurement for the acquisition of second MR data from the second section takes place with a third recording quality, and the second recording quality is higher than the third recording quality.

7. The method as claimed in claim 6, further comprising:
compiling a dental overview map as a function of the MR data and the abnormality of the at least one section of the dentition, wherein the dental overview map comprises a representation of a tooth of the examination object's dentition and a representation of the abnormality of the at least one section of the dentition; and
providing the dental overview map.

8. The method as claimed in claim 6, wherein the at least one section in which the abnormality is determined is a first section, and during the performance of the analysis of sections of the dentition, a presence of an abnormality in a second section is excluded.

9. The method as claimed in claim 6, wherein the performance of the analysis of sections of the dentition includes a determination of inflammation or dental caries.

10. The method as claimed in claim 6, further comprising:
determining a relative position between an abnormality of the at least one section and at least one tooth with the at least one section,
wherein the compilation of the dental overview map takes place as a function of the relative position between the abnormality of the at least one section and the at least one tooth.

11. A magnetic resonance (MR) apparatus comprising a computer, wherein the computer is configured to coordinate a method for compiling a dental overview map of a dentition of an examination object on the basis of MR data from a magnetic resonance measurement of the dentition, the computer configured to:
perform an MR measurement for acquiring MR data from the dentition, wherein an imaging volume of the MR measurement is matched with a volume of the dentition, and the imaging volume includes a number of teeth in the dentition;

perform an analysis of sections of the dentition, each of which includes a subset of the number of teeth in the dentition in order to determine an abnormality on the basis of the MR data, wherein an abnormality is determined in at least one section, wherein the MR measurement is a first MR measurement, the first MR measurement for acquiring first MR data from the dentition is performed at a first time point, a first imaging volume of the first MR measurement is matched with a first volume of the dentition and includes a first number of teeth, and the at least one section in which the abnormality is determined is a first section, wherein in one step, a second MR measurement for acquiring second MR data from the dentition is performed at a second time point, wherein a second imaging volume of the second MR measurement with a second volume of the dentition and includes at least one tooth and wherein at least one imaging parameter of the second MR measurement is determined as a function of the abnormality of the first section, wherein the performance of the second MR measurement for acquiring second MR data from the second section takes place with a third recording quality, and the third recording quality is lower than a first recording quality used during the performance of the first MR measurement for the acquisition of the first MR data from the first section.

12. A magnetic resonance (MR) apparatus comprising a computer, wherein the computer is configured to coordinate a method for compiling a dental overview map of a dentition of an examination object on the basis of MR data from a magnetic resonance measurement of the dentition, the computer configured to:
perform an MR measurement for acquiring MR data from the dentition, wherein an imaging volume of the MR measurement is matched with a volume of the dentition, and the imaging volume includes a number of teeth in the dentition; and perform an analysis of sections of the dentition, each of which includes a subset of the number of teeth in the dentition in order to determine an abnormality on the basis of the MR data, wherein an abnormality is determined in at least one section, wherein the MR measurement is a first MR measurement, the first MR measurement for acquiring first MR data from the dentition is performed at a first time point, a first imaging volume of the first MR measurement is matched with a first volume of the dentition and includes a first number of teeth, and the at least one section in which the abnormality is determined is a first section, wherein in one step, a second MR measurement for acquiring second MR data from the dentition is performed at a second time point, wherein a second imaging volume of the second MR measurement with a second volume of the dentition and includes at least one tooth and wherein at least one imaging parameter of the second MR measurement is determined as a function of the abnormality of the first section, and wherein the performance of the second MR measurement for the acquisition of second MR data from the first section takes place with a second recording quality and the performance of the second MR measurement for the acquisition of second MR data from the second section takes place with a third recording quality, and the second recording quality is higher than the third recording quality.

\* \* \* \* \*